US00PP10135P

United States Patent [19]

Huang

[11] Patent Number: Plant 10,135

[45] Date of Patent: Dec. 2, 1997

[54] LIMONIUM PLANT NAMED 'NEW WONDER PINK'

[75] Inventor: Ji Ming Huang, Watsonville, Calif.

[73] Assignee: Seed Investment Inc., Watsonville, Calif.

[21] Appl. No.: 699,081

[22] Filed: Aug. 19, 1996

[51] Int. Cl.[6] ..... A01H 5/00

[52] U.S. Cl. ..... Plt./68.1

[58] Field of Search ..... Plt./68.1

*Primary Examiner*—James R. Feyrer
*Attorney, Agent, or Firm*—C. A. Whealy

[57] ABSTRACT

A distinct cultivar of Limonium plant named 'New Wonder Pink', characterized by its bright flower color; large panicles; numerous flowering stems per plant; resistance to Botrytis; and good postproduction longevity.

1 Drawing Sheet

The present invention relates to a new and distinct cultivar of Limonium plant, botanically known as *Limonium sinuatum* and referred to by the cultivar name 'New Wonder Pink.'

The new cultivar is a product of a planned breeding program conducted by the inventor in Watsonville, Calif. The objective of the breeding program is to create new Limonium cultivars having large panicles, strong flower stems, strong flower color, resistant to Botrytis, and numerous flowering stems.

The new cultivar originated from a cross made by the inventor in of an unnamed proprietary seedling selection as the male or pollen parent, and the nonpatented cultivar 'New Era Pink No. 30' as the female or seed parent. The cultivar 'New Wonder Pink' was discovered and selected by the inventor as a flowering plant within the progeny of the stated cross in a controlled environment in Watsonville, Calif., in 1994.

Asexual reproduction of the new cultivar by tissue culture in a controlled environment in Watsonville, Calif., has shown that the unique features of this new Limonium are stable and reproduced true to type in successive generations.

The cultivar 'New Wonder Pink' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'New Wonder Pink'. These characteristics in combination distinguish 'New Wonder Pink' as a new and distinct cultivar:

1. Bright pink flower color.
2. Large panicles.
3. Numerous flowering stems per plant.
4. Resistance to Botrytis.
5. Good postproduction longevity with inflorescences maintaining good substance and color for more than one month in an interior environment.

Compared to the male parent, an unnamed proprietary seedling selection, the new Limonium has longer flower stems, longer panicles, and flower color is brighter pink. Compared to the female parent, the cultivar 'New Era Pink No. 30', the new Limonium has longer and stronger flower stems, larger flowers and panicles, larger and thicker leaves, the flower color is darker pink.

The new Limonium can also be compared to the nonpatented cultivar 'Flash Pink,' however the new Limonium has longer and stronger flower stems, larger flowers and panicles, more flowering stems per plant, and larger and thicker leaves.

The accompanying colored photographs illustrate the overall appearance of the new cultivar, showing the colors as true as it is reasonably possible to obtain in colored reproduction of this type.

The first photograph comprises a side perspective view of a typical flowering plant of 'New Wonder Pink'.

The second photograph comprises a close-up view of flowering panicles of the cultivar 'New Wonder Pink.'

In the following description, color references are made to The Royal Horticultural Society Colour Chart except where general terms of ordinary dictionary significance are used. The following observations and measurements describe plants grown in Watsonville, Calif., under commercial practice in polyethylene-covered greenhouses and in cultivated fields with night temperatures ranging from 10 to 20C, day temperatures ranging from 20 to 30C, and light levels ranging from 5,000 to 8,000 footcandles. Measurements and numerical values represent averages for six typical flowering stems.

Botanical classification: *Limonium sinuatum* cultivar 'New Wonder Pink.'

Parentage:

*Male or pollen parent.*—Unnamed proprietary *Limonium sinuatum* seedling selection.

*Female or seed parent.*—*Limonium sinuatum* cultivar 'New Era Pink No. 30' (not patented).

Propagation:

*Type.*—Typically by tissue culture.

*Time to rooting.*—About ten days with soil temperatures of 25C. At soil temperatures of 15C, 15 days are required.

*Rooting habit.*—Fibrous and well-branched.

Plant description:

*Appearance.*—Perennial herbaceous cut flower. Stems upright and freely branching.

*Flowering stem length.*—About 110 cm.

*Crop time.*—After rooting, plants begin producing harvestable flowering stems within three months. Plants typically stay in production for about 18 months.

*Number of harvestable flowering stems per plant.*—Per year, about 40.

*Vigor.*—Vigorous.

*Stems.*—Appearance: Winged. Aspect: Strong and erect. Length: About 1 meter. Texture: Slightly pubescent. Color: 137C.

*Foliage description.*—Leaf arrangement: Alternate. Leaf size, fully expanded: Length: 22 to 25 cm. Width: About 10 cm. Leaf shape: Ovate. Leaf apex:

Obtuse. Leaf base: Acute. Leaf margin: Serrated. Leaf texture: Leathery, adaxial surface slightly pubescent. Leaf attachment: Sessile. Venation pattern: Pinnate. Color: Young foliage abaxial surface: 143B. Young foliage adaxial surface: 143B. Mature foliage abaxial surface: 137C. Mature foliage adaxial surface: 137C. Venation abaxial surface: 155B. Venation adaxial surface: 155A.

Flowering description:

*Appearance.*—Spikelet flowers arranged on corymbose panicles. Inflorescences arise from leaf axils. Flowers persistent. Panicles 12 to 13 cm in length.

*Flowering response.*—Year round, flowering continuous under optimum temperatures.

*Postproduction longevity.*—In an interior environment, inflorescences of cut flowering stems will maintain good color and substance for at least one month in an interior environment.

*Calyx.*—Shape: Bell-shaped. Size: Length: About 8 mm. Width: About 10 mm. Margin: Serrated. Texture: Shiny, smooth, and glabrous. Color, when opening and fully open, abaxial and adaxial surfaces: Margin: 72C. Center, from distal to proximal: Color fades from 73A to 73B to 73C to 73D. Base: 155D.

*Corolla.*—Shape: Cup-shaped. Size: Length: About 2 mm. Width: About 3 mm. Apex: Obtuse. Margin: Entire. Texture: Satiny, smooth, and glabrous. Color when opening and fully open, abaxial and adaxial surfaces: 155D.

*Peduncle.*—Appearance: Winged. Aspect: Strong and erect. Length: About 12 cm. Texture: Glabrous. Color: 137C. *Flower bud.*—Shape: Elongated. Rate of opening: About one week. Size: Length: About 8 mm. Width: About 2 mm. Color: 72C.

*Sepals.*—Shape: Linear. Quantity: Five. Apex: Acute. Margin: Serrated. Texture: Leathery and pubescent. Color: Abaxial surface: 137B. Adaxial surface: 138B.

*Reproductive organs.*—Androecium: Stamen number: Five. Anthers: Shape: Ovate. Size: About 1 mm. Color: 155A. Pollen: Moderate, 155A in color. Gynoecium: Pistil number: One. Stigma shape: Trilobate. Stigma color: 155D. Style color: 155D. Style length: About 7 mm. Ovary number: One.

Disease resistance: Resistant to Botrytis.

Seed production: Seed production has not been observed

It is claimed:

1. A new and distinct cultivar of Limonium plant named 'New Wonder Pink', as illustrated and described.

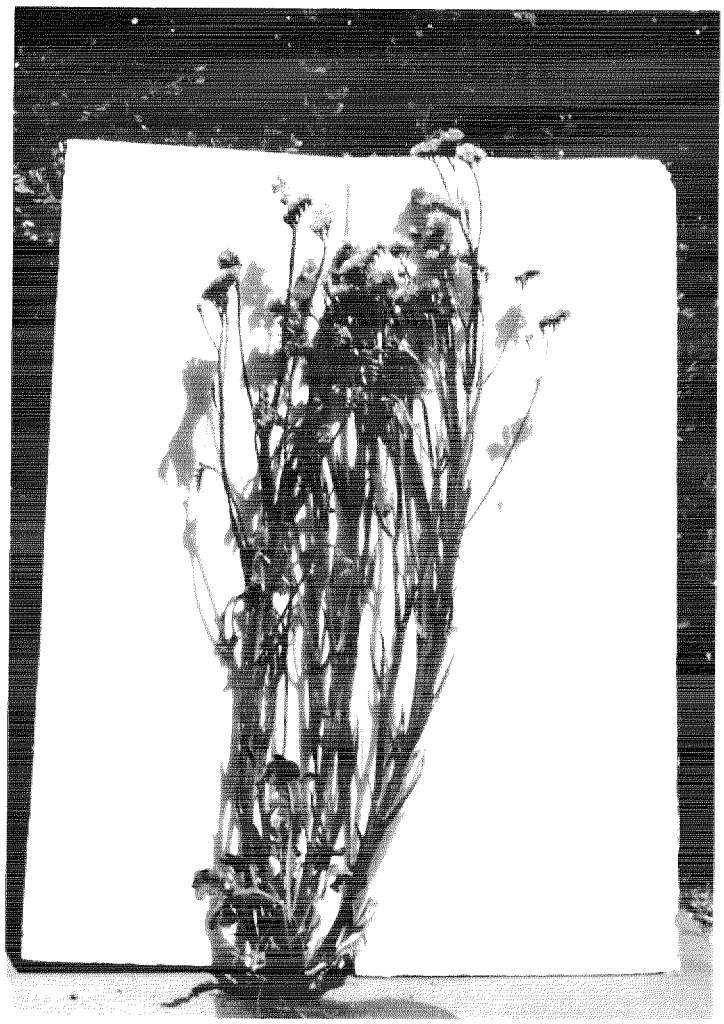
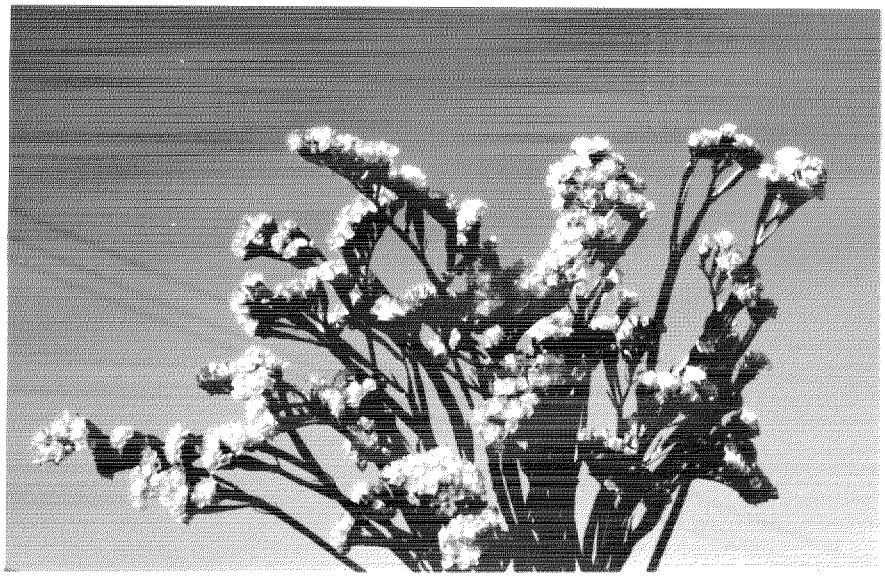

* * * * *